United States Patent
Baker et al.

(10) Patent No.: US 10,729,852 B2
(45) Date of Patent: Aug. 4, 2020

(54) WET INJECTION DETECTION AND PREVENTION SYSTEM AND METHOD

(71) Applicant: NOBLE INTERNATIONAL, INC., Orlando, FL (US)

(72) Inventors: Jeff Baker, Orlando, FL (US); Francis Michael Siemer, Orlando, FL (US); Paul van der Pol, Winter Garden, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 858 days.

(21) Appl. No.: 15/119,541

(22) PCT Filed: Feb. 17, 2015

(86) PCT No.: PCT/US2015/016213
§ 371 (c)(1),
(2) Date: Aug. 17, 2016

(87) PCT Pub. No.: WO2015/123688
PCT Pub. Date: Aug. 20, 2015

(65) Prior Publication Data
US 2017/0049965 A1    Feb. 23, 2017

Related U.S. Application Data

(60) Provisional application No. 61/940,601, filed on Feb. 17, 2014.

(51) Int. Cl.
*A61M 5/20* (2006.01)
*A61M 5/315* (2006.01)
(Continued)

(52) U.S. Cl.
CPC .......... *A61M 5/20* (2013.01); *A61M 5/31568* (2013.01); *A61M 5/31571* (2013.01);
(Continued)

(58) Field of Classification Search
CPC .. A61M 2005/2013; A61M 2005/2073; A61M 2005/208; A61M 2005/2086;
(Continued)

(56) References Cited

U.S. PATENT DOCUMENTS 6,171,276 B1 * 1/2001 Lippe ...................... A61M 5/20
128/DIG. 1
6,312,412 B1   11/2001 Saied et al.
(Continued)

FOREIGN PATENT DOCUMENTS

CN    1266373 A    9/2000
CN    1921899 A    2/2007
(Continued)

OTHER PUBLICATIONS

European Supplementary Search Report for EP Application 15748883 dated Aug. 29, 2017, pp. 1-3.
(Continued)

*Primary Examiner* — Nathan R Price
*Assistant Examiner* — Melissa A Snyder
(74) *Attorney, Agent, or Firm* — Timothy H. Van Dyke; Beusse, Wolter, Sanks & Maire PLLC (57) ABSTRACT

In an embodiment, a medicament delivery system is provided. The medicament delivery system includes a container for storing a medicament prior to use, the container having a first end and a second end, an injection member in fluid communication with the container, an actuation mechanism associated with the container and configured to deliver the medicament from the container through the injection member when the actuation mechanism is activated. The medicament delivery system further includes at least one detection element associated with the system, wherein in a first mode of operation of the system, medicament is delivered through the injection member and in a second mode of
(Continued)

operation of the system, medicament is not delivered through the injection member, and the mode of operation is dependent on an output from the at least one detection element.

25 Claims, 8 Drawing Sheets

(51) Int. Cl.
  *A61M 5/32* (2006.01)
  *A61M 5/50* (2006.01)
  *A61M 39/22* (2006.01)
  *A61M 5/31* (2006.01)

(52) U.S. Cl.
  CPC ........ *A61M 5/31578* (2013.01); *A61M 5/326* (2013.01); *A61M 5/5086* (2013.01); *A61M 39/22* (2013.01); *A61M 2005/206* (2013.01); *A61M 2005/208* (2013.01); *A61M 2005/2013* (2013.01); *A61M 2005/3125* (2013.01); *A61M 2205/13* (2013.01); *A61M 2205/3306* (2013.01); *A61M 2205/3334* (2013.01); *A61M 2205/3368* (2013.01); *A61M 2205/581* (2013.01); *A61M 2205/6018* (2013.01)

(58) Field of Classification Search
  CPC .............. A61M 5/326; A61M 2205/13; A61M 2005/3226; A61M 5/322
  See application file for complete search history.

(56) References Cited

U.S. PATENT DOCUMENTS

| | | | |
|---|---|---|---|
| 7,740,612 B2 | 6/2010 | Hochman | |
| 8,702,653 B2* | 4/2014 | Samandi | ............... A61M 5/321 604/110 |
| 2009/0216182 A1* | 8/2009 | Lauchard | ................ A61M 5/20 604/65 |
| 2010/0049126 A1* | 2/2010 | Bronfeld | ................... A61F 7/02 604/113 |
| 2011/0201998 A1 | 8/2011 | Pongpairochana et al. | |
| 2012/0078224 A1 | 3/2012 | Lerner et al. | |

FOREIGN PATENT DOCUMENTS

| | | |
|---|---|---|
| CN | 201445681 U | 5/2010 |
| WO | 2012155035 A1 | 11/2012 |
| WO | 2014/066256 | 5/2014 |

OTHER PUBLICATIONS

Baker, J. et al., International Search Report and Written Opinion, PCT/US2015/016213; dated Jun. 25, 2015; 25 pages.

English translation of Chinese Office Action in Chinese Application No. 201580019391.4, dated Jan. 23, 2019.

\* cited by examiner

WET INJECTION DETECTION AND PREVENTION SYSTEM AND METHOD

CROSS-REFERENCE TO RELATED APPLICATIONS

This application claims priority to and incorporates by reference the contents of Provisional Application No. 61/940,601 filed on Feb. 17, 2014.

BACKGROUND

Manual disposable syringe based devices have existed since the mid-1800's. These devices were designed for a single purpose of performing a subcutaneous injection through a hollow-bore needle affixed to the syringe device. Syringes are simple mechanical systems with no capability of refined fluid dynamics or ability to integrate advanced digital capabilities.

A prefilled syringe is a primary drug container and delivery system for the administration of an injectable therapy by a healthcare worker or a patient. Prefilled syringes are typically supplied to pharmaceutical customers in a ready-to-fill format for filling and packaging with a measured dose of an injectable drug or vaccine. The primary container is compliant with industry standards and pharmacopeias to ensure protection of the drug formulation over a prolonged duration.

Auto-injectors are used for self-administration by the patient outside of the healthcare system. Auto-injectors are designed to allow operators to automatically deliver the contents of a prefilled syringe at the push of a button. The auto-injector market is one of the fastest-growing segments in the medical device market. Auto-injection or "pen" devices have recently become increasingly popular for single dose or multi dose, at home self-administration. These auto-injection devices are primarily designed to accomplish two basic objectives: convenience and automation of drug delivery in an outpatient setting. These are typically mechanically spring-loaded devices that advance a component of the device to transfer medication via hollow-bore needle to a patient's tissues.

Auto-injection devices are routinely used to provide a means for self-injecting certain medications. The size and operation of these auto-injection devices can often be daunting to a patient, whether they are injecting themselves for the first or they have injected themselves before. These fears and anxieties associated with the currently available self-injection devices, particularly the auto-injection devices, may result in the administration of an incomplete dose of a medicament, failure to administer any portion of the dose of a medicament, or accidentally sticking oneself with the needle of the device, which in some instances could lead to unwanted transmission of diseases if the needle is contaminated. Furthermore, oftentimes medications are wasted when an injection device is removed from the patient mid-way through an injection before an entire dose of medicament has been received by the patient. As a result, reduced therapy compliance is also a great concern with injection devices.

Auto-injection devices lack the ability to regulate whether the medication is actually delivered to the patient or whether it is delivered to a correct location. Most auto-injection devices fail to integrate advanced digital capabilities. Therefore, there exists a need for an injection device which may be safely and efficiently used by patients without medical experience in preparing and self-injecting medications and which increases therapy compliance.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

DEFINITIONS

A "predetermined value" as used herein, for example, includes but is not limited to a value or range of values relating to an event involving use or operation of the device. These may include, but are not limited to thresholds, ceilings, baselines or range values that are desired or undesired for a particular event. Examples of predetermined values include, but are not limited to, a predetermined temperature value, predetermined time value, or a predetermined contact value, in addition to other predetermined values described herein refers to a value that is used as a reference value in relation to a value, signal, or indication that is detected by, for example, a detection element of the medicament delivery system. Predetermined value may include an optimal value, or a sub-optimal value, or any value there between. In one example, a predetermined time value may include 1 minute for resetting the system, an additional predetermined time value may include 10 seconds for resetting the system.

The term "associated" or "association", as used herein, includes but is not limited to direct and indirect attachment, adjacent to, in contact with, partially or fully attached to, and/or in close proximity therewith. The term "value" as used herein, may refer to a specific value or a range of values.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context. It is to be noted that all ranges disclosed within this specification are inclusive and are independently combinable. Furthermore, to the extent that the terms "including," "includes," "having," "has," "with," or variants thereof are used in either the detailed description and/or the claims, such terms are intended to be inclusive in a manner similar to the term "comprising."

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

The term "injection member" as used herein includes a needle or other member used to traverse the skin of a user and inject fluid there through, in one example. Various actuation mechanisms can be used to actuate the system as described herein; however, in order to effect a slow and controlled movement, a solenoid or a motorized actuation mechanism can be used, for example. However, this is not intended to be limiting, for example, "solenoid" includes, but is not limited to, a solenoid with a solenoid shaft that may interact with a plunger or stopper when it is activated, for example. Different types of actuation mechanisms known in the art and other actuation mechanisms described herein may also be used, including but not limited to ACME/lead screws, springs, compressed air, magnetic, flexinol/muscle wire, solenoids, standard DC motors, pancake motors, other motors, peristaltic pumps(s), and any other related actuation mechanisms. Actuation members as described herein refer to components of the system used to initiate actuation of the actuation mechanism(s). Examples of actuation members include, but are not limited to buttons, switches, and any other types of actuation members known to those of skill in the art.

The inventors have discovered several areas in which the prior art could be improved. Prior art injection devices and syringes have been found to lack safety and features and convenient as well as cost-saving and therapy compliance features. Oftentimes during an injection, the needle is removed from the patient before the injection is complete (or the injection is actuated before the needle is in the patient) and before the entire dose of medicament is received by the patient resulting in decreased medication therapy compliance as well as increased medication and economic waste. Therefore, the inventors herein have identified a medicament delivery system and method which solves many of these issues found in the prior art.

The subject invention includes, in one embodiment, a medicament delivery system, wherein the system includes a container for storing a medicament prior to use. The container includes a first end and a second end, an injection member in fluid communication with the container, an actuation mechanism associated with the container and configured to deliver the medicament from the container through the injection member when the actuation mechanism is activated, and at least one detection element associated with the system. Wherein in a first mode of operation of the system, medicament is delivered through the injection member and in a second mode of operation of the system, medicament is not delivered through the injection member, and the mode of operation is dependent on an output from the at least one detection element.

In a further embodiment, the system may include a controller configured to monitor the output from the at least one detection element, the controller configured to operate the system in one of the first mode of operation or the second mode of operation in response to the output received. Based on output generated by the at least one detection element, activation and/or inactivation of the actuation mechanism can be electronically controlled by the controller, in an embodiment.

In still a further embodiment, the system may include a stopper, wherein the stopper interacts with the actuation mechanism such that when the actuation mechanism is activated, the stopper traverses the container from a first position of the stopper to a second position of the stopper such that medicament is delivered through the injection member as the stopper moves from the first position to the second position. In the first position of the stopper, the injection has not yet begun and no medicament has been delivered into or through the injection member. In the second position of the stopper, the medicament dose has been completely delivered from the container through the injection member. At any point between the first position and the second position of the stopper, the delivery of medicament may be incomplete. In a single dose embodiment of the system, wherein the entire medicament contents of the container is equivalent to one dose of medicament, the second position of the stopper is at a bottom of the container. In a multi-dose embodiment of the system, wherein the container includes multiple complete doses of medicament, the second position of the stopper is at a predetermined position between the top and the bottom of the container. At this intermediate location in a multi-dose container, a full dose of medicament is provided.

The system may further include at least a first sensing element. The first sensing element can sense and provide an output based on the position of the stopper relative to the container or relative to an object outside the system. In a further embodiment, the system comprises a second sensing element. The second sensing element may be associated with the stopper such that it can sense a position of the first sensing element, or the first sensing element can sense the position of the second sensing element, such that the position of the stopper can be sensed and an amount of medicament delivered through the injection member can be sensed. In another embodiment, the at least a first or second sensing element of the system can sense and provide an output based on the position of the stopper relative to a housing within which the container is supported. In one particular embodiment, the second sensing element may include one or more magnets, in a non-limiting example, and the first sensing element may sense the one or more magnets. Such that in a non-limiting embodiment, if the second sensing element is associated with the stopper and the first sensing element is associated with the container housing (i.e., first housing or second housing) or a housing configured to receive the container, or an object outside the system, movement of the stopper relative to first sensing element will be detected by the first sensing element. Therefore, the location of the stopper can be sensed and thus, an amount of medicament delivered and/or remaining can be determined. In another non-limiting example, the first or second sensing element may include a Linear Variable Differential Transformer (LVDT), which can sense displacement of the stopper, the container and/or the injection member, for example.

In an alternative embodiment, a medicament delivery system is provided wherein the system includes a container for storing a medicament prior to use. The container includes a first end and a second end, an injection member in fluid communication with the container, an actuation mechanism associated with the container and configured to deliver the medicament from the container through the injection member when the actuation mechanism is activated, and a timer component. The system may include a controller, wherein the timer component may be a component of the controller. The timer component may detect, record, or combination thereof, events that occur with the medicament delivery system, for example, the timer component may detect a time when actuation of the system begins, the time at which medicament delivery through the injection member begins, the time at which the is delivered from the container, the time when the actuation mechanism is activated, and/or the time when the actuation member is inactivated, for example, in non-limiting embodiments. This time detected and/or recorded may be compared to a predetermined time of movement of the actuation mechanism to complete delivery of medicament, or to a predetermined time of movement of the stopper relative to the second housing of the container to complete delivery of medicament therefrom, for example In one embodiment, the system may detect a wet injection if the time detected from actuation of the system to the time the stopper ceases movement is less than the time predetermined and stored in the system for completion of an injection from actuation of the system to the time the stopper ceases movement when an injection has been fully delivered to a patient. According to this embodiment, a separate detection element is not necessary to monitor for a wet injection event.

In a first mode of operation of the system, medicament is delivered through the injection member and in a second mode of operation of the system, medicament is not delivered through the injection member, and the mode of operation is dependent on an output from the at least one detection element.

In a further embodiment, the system may include a controller configured to monitor the output from the at least one detection element, the controller configured to operate the system in one of the first mode of operation or the second mode of operation in response to the output received. Based on output generated by the at least one detection element, activation and/or inactivation of the actuation mechanism can be electronically controlled by the controller, in an embodiment.

In a further embodiment, a medicament delivery system is provided, wherein the system includes a container for storing a medicament prior to use. The container includes a first housing for containing a medicament, a stopper associated with the first housing, a second housing within which the first housing is encased, an injection member associated with a lower portion of the first housing and movable through an injection opening in the first housing, and a spring disposed between the first housing and the second housing. The system further includes a at least one detection element associated with the container and provide an output based on a condition detected by the at least one detection element, an actuation mechanism associated with the system such that when the actuation mechanism is activated, the first housing moves relative to the second housing in a first direction, the spring is biased, the injection member is extended from the second housing, the stopper moves relative to the first housing to deliver medicament through the injection member, such that when the first housing moves relative to the second housing in a second direction, the spring is released and the injection member is retracted into the second housing to prevent an unintentional contact with the injection member. In a first mode of operation of the system, the medicament is delivered through the injection member and in a second mode of operation of the system, the medicament is not delivered through the injection member, and the mode of operation is dependent on the output generated by the at least one detection element.

The at least one detection element may be provided on any portion or associated with any portion of the system, including but not limited to a lower portion of the container, or a portion of a housing of the system, a portion of the injection member, the actuation mechanism, the stopper, an inner surface of the container or an outer surface of the container, in non-limiting examples.

In a further embodiment, the at least one detection element comprises a contact sensor, wherein the output generated by the at least one detection element is dependent on whether a contact is made between the contact sensor and a patient. The contact sensor may be provided on a lower portion of the container such that removal of the container from the user signals no contact signal to the processor. In another non-limiting embodiment, the contact sensor may be placed on a housing containing the container or on a portion of the injection member or on the stopper. The contact sensor enables the system to detect if the container or the system has been removed from a target injection site of the patient during an injection in order to prevent or minimize a wet injection. In general terms, sensors may be associated with the container or the system, and may indicate or detect an amount of medicament in the container. Specific, non-limiting examples and embodiments of sensors used to make these determinations are described more fully herein.

A wet injection can include instances in which the injection member is removed from the patient while an injection is in progress (i.e., medicament flows through the injection member once the injection member is removed from the patient's body), therefore wasting medicament and preventing the patient from receiving the proper dose of medicament. Other cases of wet injections occur before the injection member is inserted into the patient and before an injection has begun, wherein the system is activated and medicament is delivered through the injection member into the environment. In an embodiment, when the system is in a second mode of operation and the stopper is disposed between the first position and the second position, an output is generated by a sensing element indicating that an incomplete delivery of medicament has occurred (i.e., a wet injection has been detected). Therefore, in embodiments herein, one or more sensing elements can sense the location of various parts of the system relative to various other parts, for example as described herein, in a non-limiting example, a first sensing element associated with a first or second housing of the container can sense a location or position of a second sensing element associated with the stopper. This information can be used to identify an amount of medicament remaining in the container or delivered from the container. In another embodiment, if the injection member has been removed from the patient, and the stopper is in motion, the system may detect a wet injection has occurred or is going to occur and delivery of medicament from the container is halted.

In one embodiment, the at least one detection element is associated with the injection member, wherein the at least one detection element includes a sensor, and the sensor is configured to detect a difference between the pressure of air and pressure of skin of a patient (e.g., a pressure sensor) to detect whether the injection member has been injected into the patient. An output is generated by the sensor to indicate to the system to stop activation of the actuation member or stop movement of the stopper or to prevent the flow of medicament through the injection member in any of the methods described herein to prevent a wet injection if the at least one detection element detects that the injection member is not in the patient and the actuation member has been activated.

In another embodiment of the system, the medicament delivery system includes a flow of electricity through the injection member such that when a change in an electrical property is detected the second mode of operation is initiated. In a further embodiment, a change in a unit of measurement on the injection member is detected by the detection element as the injection member is inserted into or removed from a patient, and wherein the mode of operation is dependent on a value of the unit. Examples of electrical properties described herein include, but are not limited to, electromagnetic properties, ultrasonic, sonar, and temperature properties. In some instances the detection element may be a component of or associated with the injection member. In other instances the injection member may be the detection element. Therefore, the electrical properties may be detected via the injection member in non-limiting embodiments.

In a further embodiment of the medicament delivery system, the at least one detection element may include a light sensor. The output from the at least one detection element may be dependent on whether a light beam is projected from the container and detected by the light sensor in one example which could indicate that a wet injection has occurred or is about to occur. In another example, projection of a light beam from the system may be visually identified by the user or patient of the system to detect whether a wet injection may occur or is occurring. In still a further embodiment, the system may be configured to stop or halt a flow of medicament if the light beam is projected from the system.

In yet a further embodiment, the at least one detection element may include a temperature sensor which can identify or detect a temperature of the skin of a patient or an internal temperature of a patient in non-limiting embodiments. The output of the at least one detection element may be dependent on a temperature detected by the temperature sensor. In one particular embodiment, the system may operate in the first mode of operation when the temperature sensor detects a temperature of the patient between 87 and 100 degrees Fahrenheit. In another embodiment, the system may operate in the first mode of operation when the temperature sensor detects a temperature between 90 degrees Fahrenheit and 93 degrees Fahrenheit. In still a further embodiment, the system may include a contact sensor and a temperature sensor in which the mode of operation of the system is dependent on an output generated by the at least one detection element based on the contact sensor and the temperature sensor. In a non-limiting example, the system may require that contact be detected by the contact sensor and that a temperature of a particular degree range be detected by the temperature sensor to detect that the system is in contact with a patient and not an inanimate object, for example, in order to prevent a wet injection.

In still a further embodiment, the at least one detection element includes a proximity sensor to detect a proximity of the system to a target area of a patient. The mode of operation of the system may depend on the output generated by the at least one detection element based on the proximity of the system to the target area. The target area of a patient may include an intended injection area and areas adjacent to the intended injection area. The target area of a patient may depend on the type of medicament being injected, for example. The target area of the patient may change from one injection to the next based on the need to move injection sites in instances where many injections are being performed in one general area of a patient in order to reduce trauma and/or pain to that particular area, for example.

The container may include an electrical current directed therethrough in order to detect an amount of medicament therein, in an embodiment. This is useful, for example, wherein a wet injection occurs and is detected by the system, and an amount of medicament remaining in the container needs to be measured to determine how much medicament was delivered to the patient and how much of the complete dose remains. In some embodiments, once a wet injection is detected, the user must replace the container of the system with a new container and/or a new needle to complete the dose of the medicament. The identification of the amount of medicament remaining in the container is therefore very helpful in determining the amount of medicament required to complete the required dose. The system then identifies an amount of the medicament in the new container required to be injected to complete the dose.

In another embodiment, the system may include one or more valves. The one or more valves may be configured to open and close in response to output generated by the at least one detection element. In one instance, when the valve is open, medicament is delivered through the injection member, and when the valve is closed, delivery of medicament through the injection member is halted.

The injection member may be associated with the container such that it is extended from the container upon activation of the actuation mechanism, and retracted into the container after use. It is contemplated herein that a number of different variations of retraction mechanisms can be used. For example, a tension spring can be associated with a second housing of the system (described in a further embodiment discussed below) and a portion of the first housing, wherein the spring could be used to move the first housing relative to the second housing in a second direction to retract the injection member. Another embodiment may include an actuation mechanism which attaches onto or associates with the stopper or the first housing so as to retract the first housing. Retraction of the injection member serves to provide a safety mechanism to prevent a user from sticking themselves with the injection member before, during, or after an injection event. In an embodiment, the retraction may occur if the injection mechanism is extended from the container before the injection or delivery of medicament has begun, during an injection if the injection member is removed from the patient, and/or after an injection has been completed.

In some embodiments described herein, the injection member is extended from the container when the actuation mechanism is activated and the system is in a first mode of operation, and the injection member is retracted into the container when the system is in a second mode of operation.

In a further embodiment of the system, an obstruction member is provided, wherein upon retraction of the injection member into the container the obstruction member obstructs (blocks or covers over) the injection opening such that extension of the injection member there through is prevented. This is a safety feature to prevent unwanted sticks of the user with the injection member.

In still a further embodiment, a locking mechanism is associated with the actuation mechanism, wherein the locking mechanism is initiated (initiation of the locking mechanism may include locking or unlocking of the locking mechanism, depending on the output received) in response to the output generated by the at least one detection element. When the locking mechanism is in a locked position, delivery of medicament through the injection member is prevented, and when the locking mechanism is in an unlocked position, medicament is delivered through the injection member. The locking mechanism controls initiation of the delivery of medicament, i.e., whether the system will enter a second mode of operation.

In yet a further embodiment, the system includes a stopping mechanism, wherein the stopping mechanism may be activated in response to an output generated by the at least one detection element and in a further embodiment, the at least one detection element and the at least one sensing element, wherein the stopping mechanism is configured to halt delivery of the medicament after the actuation mechanism has been activated and before delivery of the medicament is complete. In an embodiment, delivery of the medicament is complete when a full dose has been delivered through the injection member. The system may be adapted for use with either or both of single-dose and multi-dose injections. While in single-dose injections, the container is empty once the full dose has been delivered, however, in multi-dose injections, the container may contain other subsequent doses of medicament even after a full dose has been delivered through the injection member. The various ways in which the stopping mechanism functions include, but are not limited to, stopping a motor of the system, stopping a spring in the system or other component of the system from functioning or moving by way of a brake, and numerous other mechanical and electrical ways of stopping the delivery of medicament from the container as are known to those of skill in the art.

In an embodiment, a motor is configured to drive the system. The processor may be associated with the stopper and the motor associated with either the first housing and/or the stopper, such that when the detection element detects no contact between the patient and the detection element, the processor stops the motor from moving the first housing in a first direction relative to the second housing and/or the stopper in a first direction relative to the first housing to prevent the medicament from being delivered through the injection member. In addition to, or in place of a detection element used to detect contact or lack thereof between the user and the container or system, other means to detect contact known in the art are contemplated herein including, but not limited to contact sensors or contact switches. In a further embodiment, as discussed herein, at least a first sensing element and a second sensing element can be used to detect an amount of medicament remaining in the container, whereby an output may be generated by the first or second sensing element, such that the mode of operation of the system is dependent on the output. The mode of operation of the system may be dependent on both an output from the detection element and an output from one or more sensing elements of the system in an embodiment. Consequently, both injection member location (relative to the patient) as well as amount of medicament in the container can be detected or sensed and as a result, the mode of operation of the system can be determined, in an embodiment.

In another embodiment, the system may further include a flow of electricity through the injection member such that when a change in an electrical property is detected the second mode of operation is initiated. Examples of electrical properties described herein include, but are not limited to, electromagnetic properties, ultrasonic, sonar, and temperature properties. In a further embodiment, a change in a unit of measurement on the injection member may be detected as the injection member is inserted into or removed from the patient. The mode of operation of the system may be dependent on a value of the unit of measurement detected.

Once a wet injection has been detected, the system provides rehabilitative processes in an embodiment. The amount of medicament remaining to complete a dose of medicament can be identified. An amount of medicament remaining in the container may be identified based on the amount of displacement of the stopper within the container after a wet injection is detected in one embodiment, and as described herein, this can be sensed with the first and second sensing elements or by other means described herein. In another embodiment, when the system is in a second mode of operation and the stopper is between the first position and the second position, a number of turns of the motor may indicate an amount of medicament remaining in the container. The motor can be actuated in a number of manners including activation by the actuation mechanism, by contact with a user, with a button or switch, or automatically following a series of steps, or by any other means known to those of skill in the art.

In another embodiment, the system may include a flow sensor in order to detect the amount of medicament delivered through the injection member, and may therefore provide information relating to the amount of medicament remaining in the container. The flow sensor may be provided in the injection member, adjacent to the injection member, or in the container in non-limiting examples. In still a further embodiment, the amount of medicament remaining in the container can be identified with a visual indicator of the system. The visual indicator may include a window provided to allow a user to view the amount of medicament remaining or the position of the stopper, for example. In another embodiment, the visual indicator includes a series of lines or indications on the container, lights or a screen associated with the system, or a change in color of at least a portion of the system or container in order to indicate the amount of medicament remaining in the container or that the medicament dose has been completely delivered from the container.

Once the system is in the second mode of operation, in an embodiment, it is automatically reset or is configured to be manually reset such that any remaining medicament in the container can be delivered through the injection member, in an embodiment. Reset may include, but is not limited to, the unlocking of the locking mechanism, inactivation of the stopping mechanism, in non-limiting examples. In one particular example, the locking mechanism can automatically reset to the unlocked position following a predetermined time period. This predetermined time period may be set by the user of the system prior to using the system, or may be preset by the manufacturer of the system, for example. The predetermined time period may range between one (1) second and ten (10) minutes in one embodiment, or between five (5) seconds and five (5) minutes in a further embodiment.

In another embodiment, following the second mode of operation, the system can be configured for reset wherein the container may be replaced with a new container for purposes of completing a dose of medicament, or in order to begin a new medicament dose. In yet another embodiment, the system may be reset to begin the first mode of operation upon activation of the actuation mechanism or upon insertion of a container, in non limiting examples. The reset of the system may be automatic or manual.

In yet a further embodiment, the system described herein can be activated by a peristaltic pump actuation mechanism by which the medicament can be contained within a flexible container, and a roller attached to a rotor which compresses the flexible container so as to displace the medicament from the container such that it is delivered through the injection member. As the rotor turns, the part of the container under compression is occluded by the roller and the medicament within the container is forced to be pumped to move through the tube and through the injection member. Once the container is opened to its natural state, fluid flow is induced to the pump. In some embodiments, two or more rollers may occlude the container and trapping a body of medicament between them. The medicament can then be transported toward the pump outlet, in one example.

The detection element described herein may be integrated into, associated with, adjacent to, or on the injection member in certain embodiments.

In an embodiment, a method for preventing a wet injection from occurring during a patient injection with a medicament delivery system comprising an injection member and a first container containing a medicament dose is provided. The method includes sensing an amount of medicament in the container, such that an incomplete dose of medicament can be detected, detecting a removal of the injection member from the patient when a medicament dose is incomplete, halting a flow of the medicament through the injection member when the injection member is removed from the patient and the medicament dose is incomplete, and providing an indication to the patient to rehabilitate the system to complete the medicament dose.

In a further embodiment, the removal of the injection member form the patient can be detected via a visual observation, one or more sensors, a change in an electromagnetic property, or one or more switches. In an embodiment, the flow of medicament through the injection member is halted via one or more valves, a brake, or an electrical stop signal.

In a further embodiment, an indication to the patient to rehabilitate the system comprises a series of stepwise instructions audibly provided to the patient by the system. The stepwise instructions may be provided via a speaker associated with the system. In another embodiment, the indication to the patient to rehabilitate the system comprises one or more visual indications to the patient. Visual indications may be provided as described herein, including but not limited to a light or series of light indicators, a window providing a view into the system or container such that a user can identify the amount of medicament remaining or delivered, or a screen or display providing information regarding the amount of medicament remaining or delivered from the container, for example.

In a further embodiment, the indication to the patient to rehabilitate the system comprises an indication to replace the first container with a second container and activate the system to inject a calculated medicament dose amount substantially equivalent to the medicament dose remaining in the first container. In another embodiment, the rehabilitation of the system to complete the medicament dose comprises providing an indication to the patient to re-insert the injection member into the patient and activate the system to complete the medicament dose remaining in the container. In yet another embodiment, the rehabilitation of the system to complete the medicament dose comprises replacing the injection member and providing an indication to the patient to insert the injection member into the patient and activate the system to complete the dose remaining in the container.

In still another embodiment, a medicament delivery system as described in embodiments herein is provided, wherein based on the output generated by the detection element, information about the detection is provided to the system, and the medicament continues to be delivered through the injection member. For example, if a wet injection is detected, the system is notified, but the injection continues in one non-limiting embodiment.

For example, in a non-limiting embodiment, a medicament delivery system is provided including a container for storing a medicament prior to use, the container having a first end and a second end. An injection member is in fluid communication with the container, an actuation mechanism being associated with the container and configured to deliver the medicament from the container through the injection member when the actuation mechanism is activated, and at least one detection element is associated with the system, wherein the at least one detection element is configured to detect when the injection member is removed from a patient during medicament delivery through the injection member.

Figure 1:
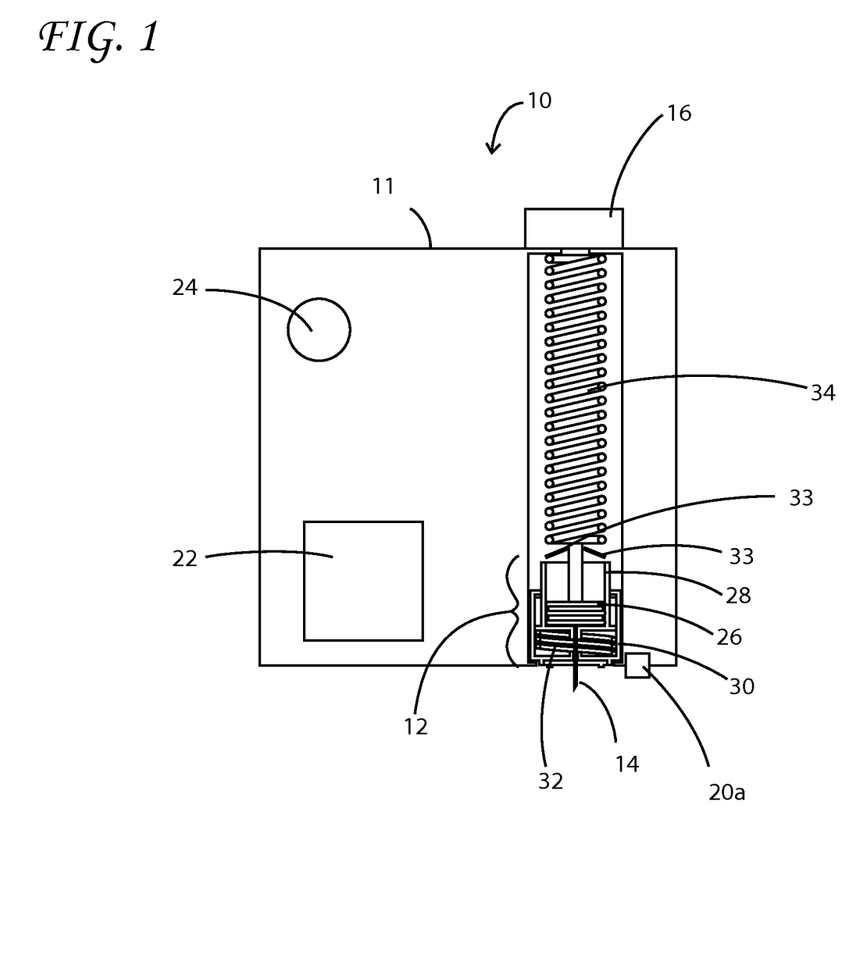
FIG. 1 provides a cross sectional view of an embodiment of a medicament delivery system.

Turning to the drawings, FIG. 1 provides a cross sectional view of an embodiment of the medicament delivery system 10, including an actuation member 16 which activates the system 10, a speaker 24, a controller 22 and housing a container 12. The medicament delivery system 10 is in a first mode of operation and an injection member 14 is delivered from the container 12. A first spring 32 and a second spring 34 are biased to allow delivery of the injection member 14 from the container 12 and to provide movement of the stopper 26 in a first direction relative to the second housing 28 to deliver medicament within the container 12 through the injection member 14 based on output provided to the controller 22 from the detection element (i.e., contact sensor 20a) on the housing 11. The detection element 20 may generally include an electromechanical element, in an embodiment. Interconnection between the actuation mechanism(s) 17, actuation member(s) 16, controller (22) and other various parts of the system along with the connectivity there between are as described in U.S. patent application Ser. Nos. 61/788,033, 14/017,933, and 61/886,596. One skilled in the art would understand the interconnectivity and function between the motor, controller, actuation mechanism and other parts of the system in view of the teachings of these applications. One skilled in the art would also understand that communications between the components of the system, including the detection elements, the actuation members, the controller, for example, can occur wirelessly or through a wired connection as known in the art. The stopper 26 is shown in a second position within the container 12. A detection element 20 is provided on a lower portion of the housing 11 of the system 10. In this embodiment, the detection element includes a contact sensor 20a, but in other embodiments may include a light sensor 20b (as shown in FIG. 2), or a temperature switch 20c (as shown in FIG. 3), in non limiting examples.

A brake (33) is provided in the system 10 of FIG. 1, wherein based on the output received from the detection element 20, the brake 33 may be initiated to halt movement of the stopper, and therefore prevent further delivery of medicament through the injection member 14. This occurs, for example, when a wet injection is detected by the system in order to prevent delivery of medicament from the system when the injection member is not inserted into the user, in one embodiment. Therefore, when a wet injection is detected via the detection element 20, the brake 33 engages the shaft of the stopper 26, preventing movement of the stopper 26 relative to the second housing 28 to prevent medicament from flowing through the injection member 14.

Figure 2:
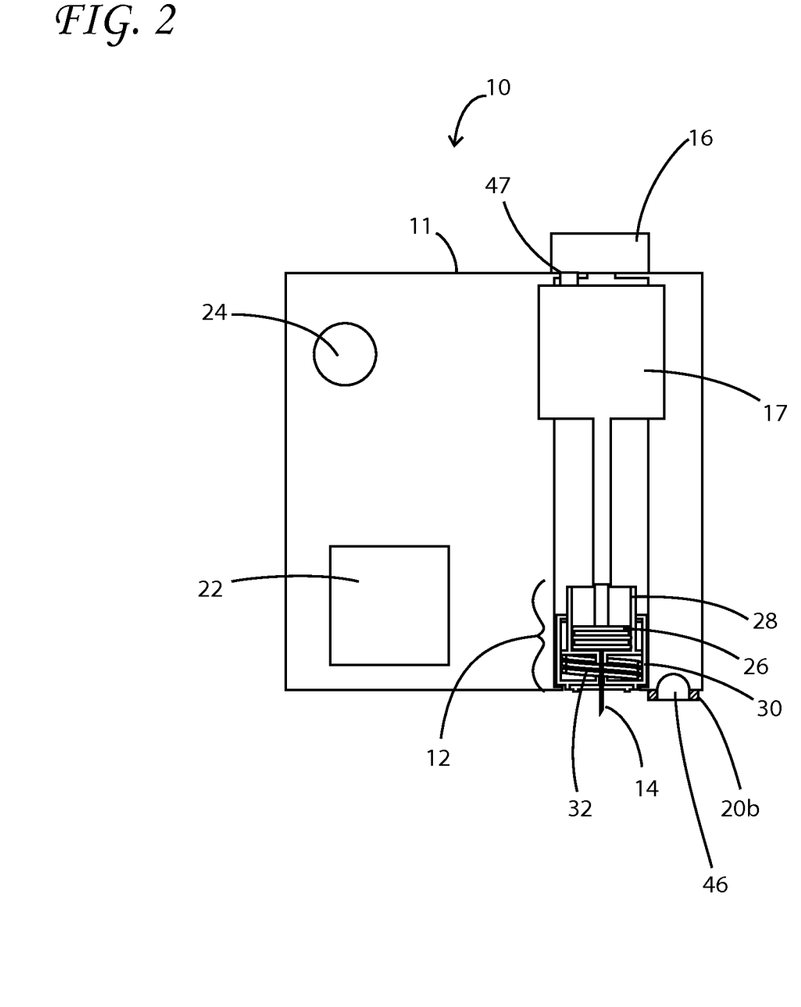
FIG. 2 provides a cross sectional view of another embodiment of a medicament delivery system.
Figure 3:
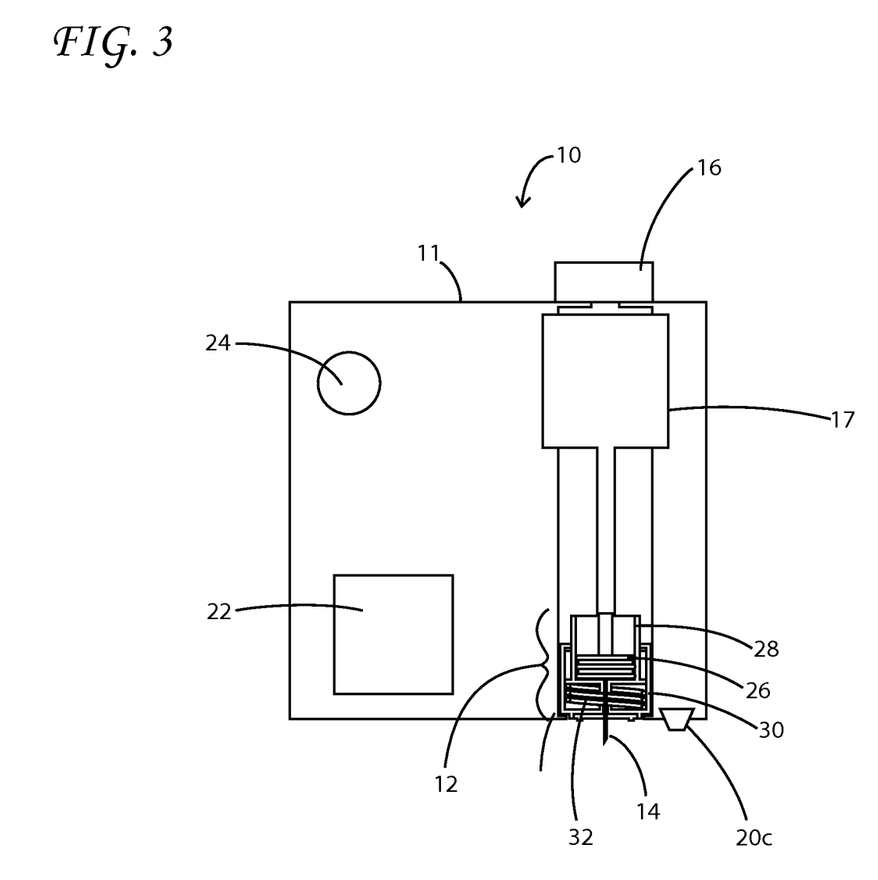
FIG. 3 provides a cross sectional view of a further embodiment of a medicament delivery system.

FIG. 2 shows a cross section of another embodiment of the system 10 having a housing 11 and an actuation mechanism 17 which can be activated by the actuation member 16. The actuation mechanism 17 in the embodiment provided in FIG. 2 shows a motor and a drive shaft component which drive the movement of the stopper 26 relative to the container 12 to control movement of the stopper 26 relative to the second housing 28 and movement of the second housing 28 relative to the first housing 30, or vice versa.

FIG. 2 provides a detection element embodied as a light sensor 20b. The light sensor 20b can detect light emanating from a light source 46 when the container and/or the housing 11 is not in contact with the user. When the housing 11 is in contact with a target surface of a user, light emanating from the light source 46 is obstructed, and not detected by the light sensor 20b. The light source 46 is shown as in contact with a bottom surface of the housing 11; however, the light source may be provided within or disposed on a portion of the container 12 such that when a lower surface of the housing 11 is not in contact with a surface of a user, light may emanate from the light source 46, in an embodiment. In another non-limiting embodiment, the light sensor 20b may detect a reflection of light from the light source 46 off of a surface of a user when the housing 11 is not in contact with the surface of the user. In response to detection of light by the light sensor 20b, an output is generated to the system 10 to detect, or to detect and prevent or halt delivery of medicament through the injection member 14 to detect or detect and prevent a wet injection. FIG. 2 includes a locking mechanism 47, wherein the locking mechanism prevents delivery of medicament through the injection member when the locking mechanism 47 is in a locked position. This prevention is in response to an output generated by the at least one detection element, e.g., the light sensor 20b, for example. Consequently, if the housing 11 is not against a surface of a user in position for injection, a light emanating from the light source 46 is detected by the light sensor 20b, and the locking mechanism 47 remains in a locked position so as to prevent delivery of medicament through the injection member (i.e., maintains the system 10 in a second mode of operation).

FIG. 2 includes a locking mechanism 47, wherein the locking mechanism prevents delivery of medicament through the injection member when the locking mechanism 47 is in a locked position. This prevention is in response to an output generated by the at least one detection element, e.g., the light sensor 20b. Consequently, in one non-limiting example, if the light sensor 20b detects light emanating from light source 46 and/or reflecting off of a surface from light source 46, the locking mechanism 47 may remain in a locked position.

FIG. 3 is a cross-sectional view of an embodiment of the system 10 having a housing 11, and a container 12 there within. A controller 22 and a speaker 24 are provided on the system 10, and an actuation member 16 is associated with the system 10. The actuation member 16 is provided to activate the actuation mechanism 17 shown as including a motor and a drive shaft component which drive movement of the stopper 26 relative to the container 12, for example. In the embodiment shown in FIG. 3, a temperature switch 20c is disposed on a portion of the housing 11 so as to detect temperature of a surface that is associated with the temperature switch 20c. This is one non-limiting example of a method to detect at wet injection by detecting if the system 10 has been displaced from a surface of a user during an injection.

Figure 4A:
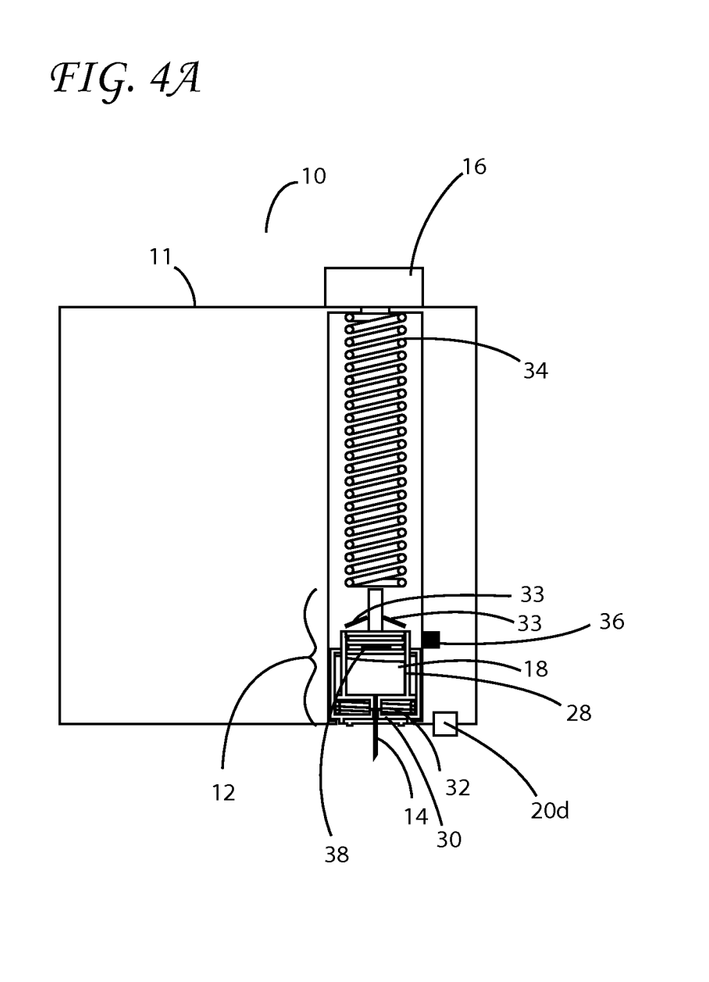
FIGS. 4A-4B provide a cross sectional view of another embodiment of a medicament delivery system in a first mode of operation, and a second mode of operation, respectively.
Figure 4B:
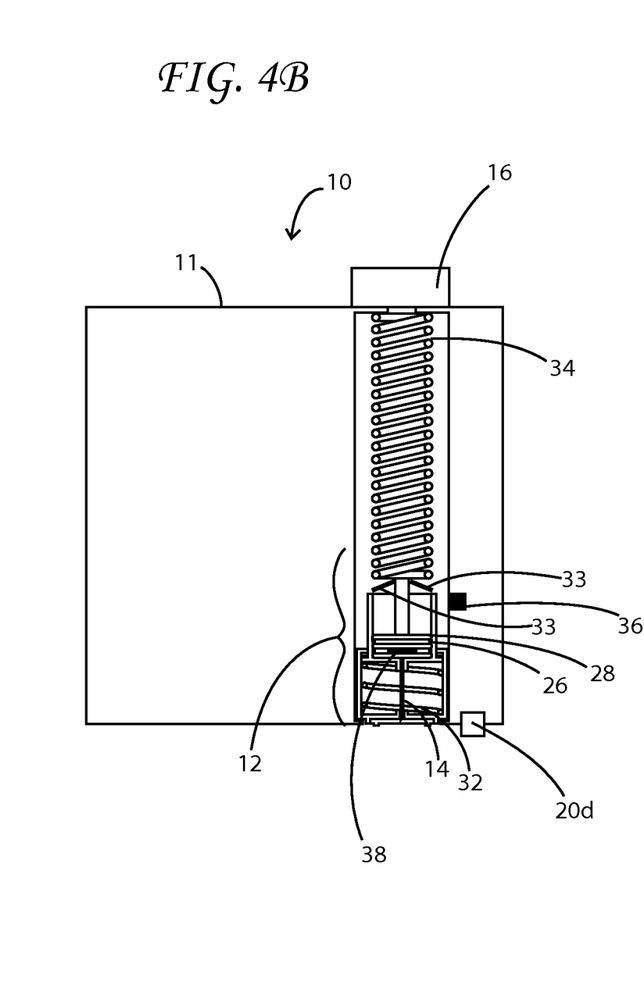

FIGS. 4A-4B illustrate the system 10 in a first mode of operation (FIG. 4A) and second mode of operation (FIG. 4B), wherein medicament 18 is in the container 12 of FIG. 4A, and the second spring 34 which drives the stopper 26 is unbiased. In the first mode of operation of the system 10 medicament is delivered through the injection member 14 after activation of the system by way of the actuation member 16 as shown in FIG. 4A. The second spring 34 includes a greater resistance than the first spring 32, in a non-limiting embodiment, such that by activating the actuation member 16, the first spring 32 is compressed before the second spring 34 and the injection member 14 traverses the first contaminant barrier 29 (shown in FIG. 5) in the first housing 30 before the medicament 18 is delivered from the injection member 14. The system 10 can compensate for different forces required to inject for delivery of a medicament 18 using the system 10. In one example, one force may be needed to force a needle to puncture the skin of a user with the system 10, wherein another force may be needed to disperse/deliver a medicament 18 from the system to a user. The subject invention can vary to compensate for these different forces. In one embodiment, springs of varying resistances may be used. Based on an output generated by the detection element (i.e., contact sensor 20d), the system 10 may transition to the second mode of operation wherein no medicament is delivered through the injection member 14 in order to prevent a wet injection, and in certain embodiments, the injection member 14 is retracted into the first housing 30 to prevent unintentional contact with the injection member 14 as shown in FIG. 4B.

In some embodiments, the wet injection detection and prevention is based, in part, on the detection by the detection element 20 and in part on a first and second sensing element. FIGS. 4A-B provide a first sensing element 36 as being disposed on a portion of the system 10, and a second sensing element 38 as associated with the stopper 26 such that the position of the stopper 26 relative to the first sensing element 36 can be identified as the first sensing element 36 senses the position of the second sensing element 38 relative to the first sensing element. In non-limiting embodiments the second sensing element 38 may be formed as part of the stopper or embedded in the stopper. The first sensing element 36 can generate an output to the system 10 or to the user including information about the position of the second sensing element 38, or vice versa, in non-limiting embodiments. This information is useful in determining an amount of medicament 18 that has been delivered through the injection member 14 in order to determine whether a full or partial dose has been given, and determine an amount of the dose remaining to be given to the user.

In the embodiment shown in FIGS. 4A-B, when the contact sensor 20d of the system 10 detects that contact has been removed between the user and the contact sensor 20d, an output can be sent from the contact sensor 20d (one example of the detection element 20) to the system. In an embodiment, when the first sensing element 36 senses a position of the second sensing element 38, the second element is associated with the stopper 26, and the stopper 26 is in a position between a first position and a second position, and no contact between the contact sensor 20d user is detected by the contact sensor 20d, the system 10 can detect that a wet injection has occurred, the injection can be stopped (i.e., system in the second mode of operation) by one of the methods described herein. Methods of stopping the injection include, but are not limited to initiating the break 33 to stop movement of the stopper 26. For example, a signal can be initiated to activate the break which can prevent the stopper 26 from moving. In one non-limiting example, the break 33 could operate by engaging a portion of the stopper 26 (i.e., the shaft) by grasping the shaft upon sensing a wet injection has occurred or is about to occur. There are various ways known in the art to stop or prevent continued delivery of medicament through the injection member. Alternatively, one can stop delivery of medicament by ceasing activation of the system 10. In other embodiments as depicted in FIGS. 2-3, once a wet injection has been detected, an output is sent to the controller 22, which in turn provides an output to the actuation mechanism 17 to stop, for example, in embodiments which include a motor as part of the actuation mechanism 17.

Figure 5:
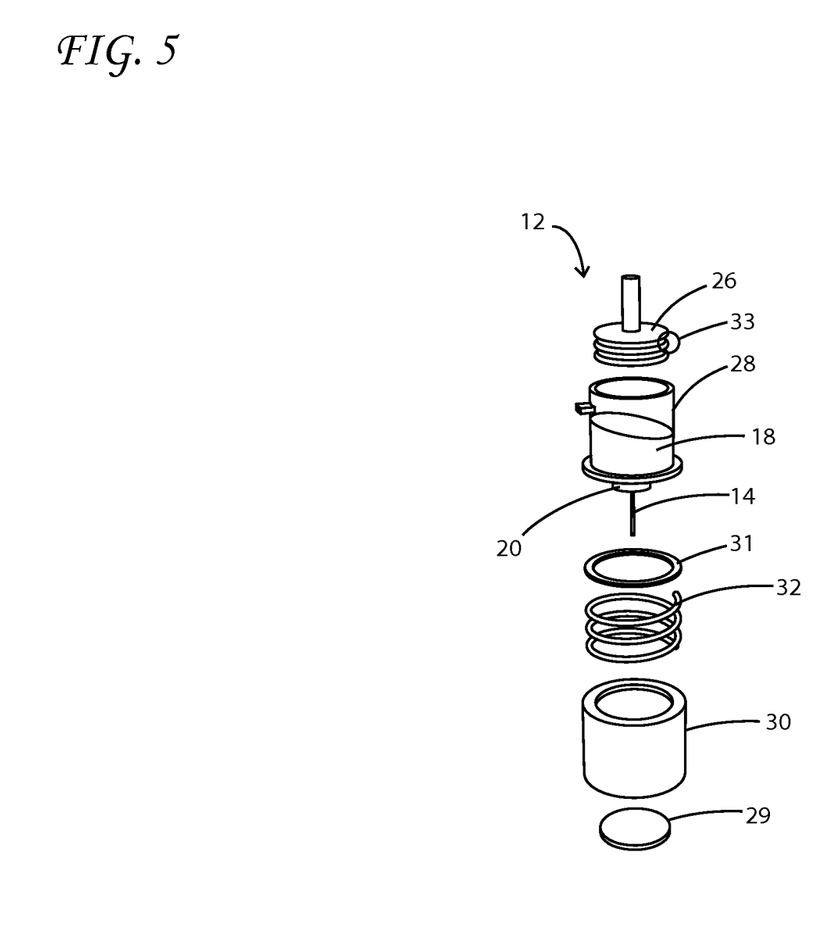
FIG. 5 provides an exploded view of an embodiment of a container.
Figure 6:
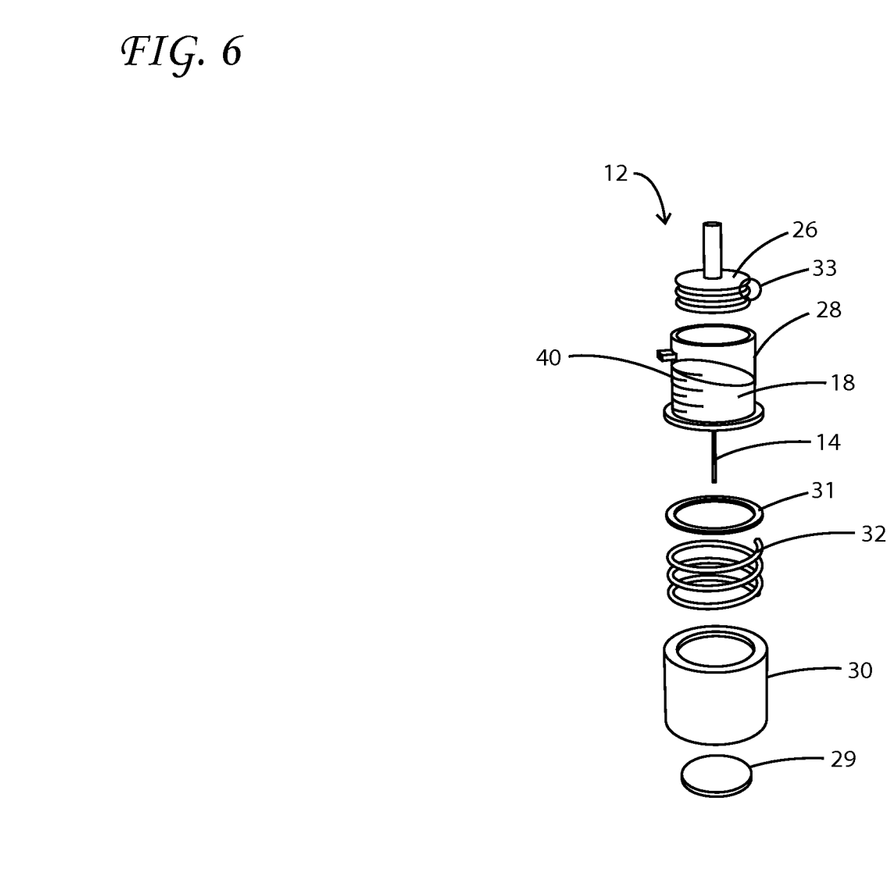
FIG. 6 provides an exploded view of another embodiment of a container.

FIGS. 5 and 6 provide exploded views of the container 12, illustrating the locations of the first contaminant barrier 29, second contaminant barrier 31 and third contaminant barrier 33 to seal the container 10 and maintain sterility of the medicament 18 there within. FIG. 5 provides a detection element 20 embodied as a sensor adjacent to the injection member 14. The detection element 20 provides an output based on the location of the detection element 20 relative to a target area of a user. Based on output received from the detection element 20, the system operates in the first or second mode of operation. An embodiment of a visual indicator 40 is displayed on the second housing 28 in FIG. 6, such that a user can determine an amount of medicament 18 within the container 12 by way of the visual indicator 40. Various embodiments of visual indicators 40 are further described herein.

Figure 7:
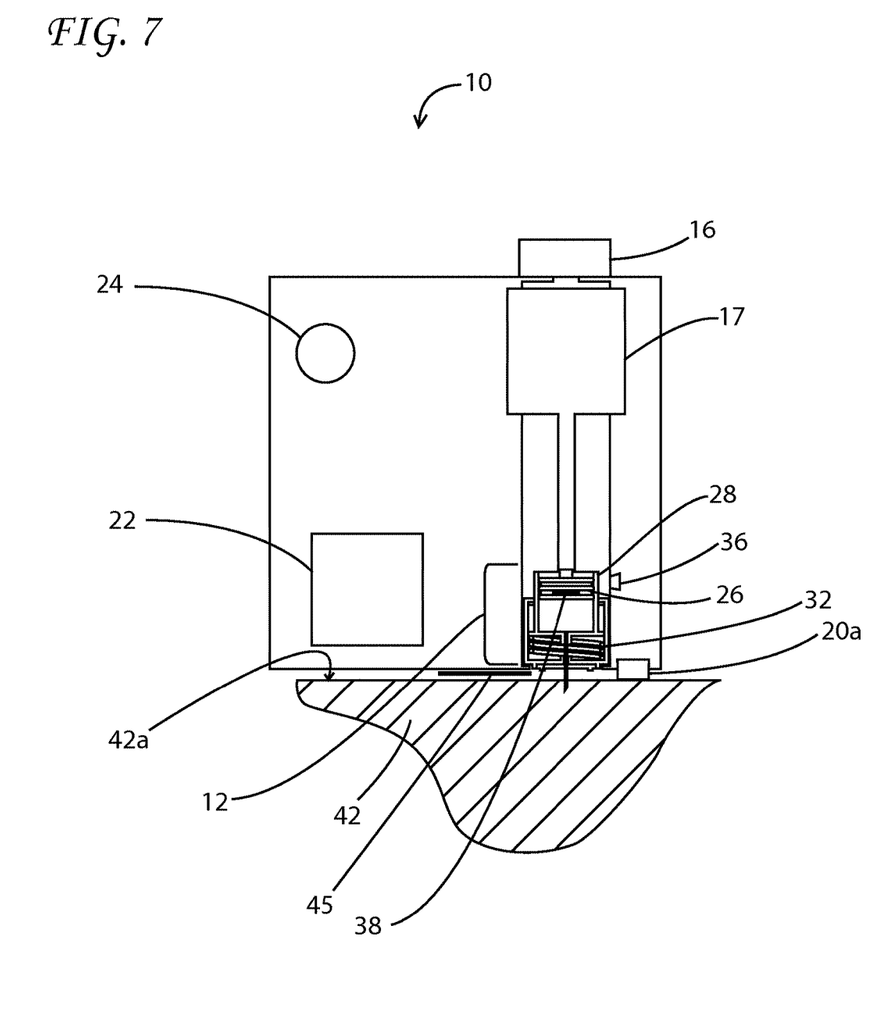
FIG. 7 is a cross sectional view of an embodiment of a medicament delivery system in use, wherein an injection member is in a target tissue of a patient during an injection.
Figure 8:
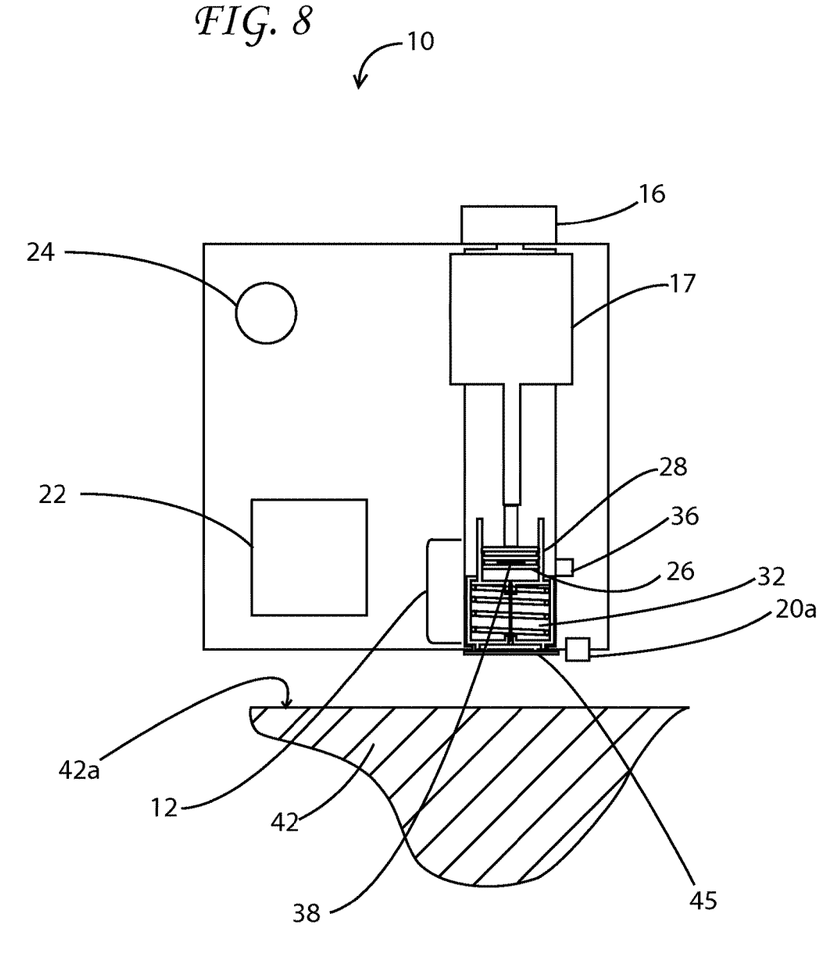
FIG. 8 is a cross sectional view of the embodiment of the medicament delivery system of FIG. 7, wherein the medicament delivery system has been moved such that the injection member has been removed from the tissue of the patient during the injection.

FIGS. 7-8 provide cross-sectional views of stepwise use of an embodiment of the system 10 as described herein. FIGS. 7 and 8 provide a system 10 embodiment having a controller 22, a speaker 24, an actuation member 16, an actuation mechanism 17, a container 12 having a first and second housing, 30, 28, a stopper 26, a first biasing member 32 disposed between the first and second housings 30, 28, a detection element (contact sensor 20a) disposed on a portion of the housing 11 of the system 10 to detect contact between the contact sensor 20a and a surface (i.e., a target surface 42a of a target tissue 42 of a user). The sensing elements 36, 38 are provided to detect the position of the stopper 26 during use of the system 10 and can be used to detect an amount of medicament remaining in the container 12 during an injection and particularly, if a wet injection is detected by the system 10. Detecting an amount of medicament remaining in the container 12 following a wet injection can provide information as to an amount of medicament remaining to be provided to a user after a wet injection is detected, or detected and prevented. FIG. 7 shows an obstruction member 45 associated with a lower portion of the housing 11 of the system 10. The obstruction member 45 may be a sliding member, wherein it slides, for example, to cover the opening through which the injection member 14 exits the container 12 in a non-limiting embodiment as shown in FIG. 7, to prevent unwanted sticks by way of contact with the injection member 14 when the container 12 is removed from the housing 11. In FIG. 8, the injection member 14 is shown as retracted into the container 12, and the obstruction member 45 covers over the injection opening to prevent extension of the injection member 14 there through, and/or insertion of an object in through the opening to contact the injection member 14. In other non-limiting embodiments, a portion of the obstruction member 45 may hinge from the housing to allow passage of the injection member 14 there through. Other mechanisms for causing the obstruction member to close FIG. 8 shows the system 10 being removed from the user such that the contact sensor 20a is displaced from the target surface 42a of the target tissue 42 of the patient, wherein a wet injection is detected and prevented by the system 10. Once the wet injection is detected, the injection member 14 is retracted back into the container 12 so as to prevent an accidental sticking of the user with the injection member 14 and/or to preserve the sterility of the injection member 14. This may occur by way of the biasing member 32. The first and second sensing elements 36, 38 can detect the position of one another so as to identify an amount of medicament delivered to the user and/or an amount of medicament remaining in the container 12.

Following detection and prevention of a wet injection, the system 10 may provide instructions to the user to rehabilitate the system 10 in order to complete the injection. This rehabilitation may include re-activating the system 10 by way of the actuation member 16 to re-inject the user at the target surface 42a of the target tissue 42 to complete the injection and deliver the remaining portion of the medicament to the user, in one embodiment. In another embodiment, rehabilitation may involve removal of the partially used container 12 and replacement with a new container 12 for use to deliver the remaining portion of medicament, for example. A determination of the amount of medicament remaining in the previous, partially used container 12 following the wet injection is critical to rehabilitation and delivery of a remaining portion of medicament after inserting a new container 12 into the system 10. In another non-limiting embodiment, following detection and prevention of a wet injection, the partially used container 12 may be reused to complete the injection; however, a user may need to replace the used injection member 14 with a new injection member 14 prior to completing the injection, for example.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A medicament delivery system, comprising:
a container for storing a medicament prior to use, the container having a first end and a second end;
an injection member in fluid communication with the container;
an actuation mechanism associated with the container and configured to deliver the medicament from the container through the injection member when the actuation mechanism is activated; and
at least one detection element associated with the system; wherein the at least one detection element is configured to detect a condition, the condition being removal of the injection member from a patient during medicament delivery through the injection member, and
at least one sensing element or a timer component, or both, to detect incomplete medicament delivery upon a detection of removal of the injection member from the patient during medicament delivery through the injection member via the at least one detection element.

2. The medicament delivery system of claim 1, wherein the system stores information about the condition.

3. The medicament delivery system of claim 1, wherein the at least one sensing element is configured to detect an amount of medicament remaining in the device upon a detection of incomplete medicament delivery.

4. A medicament delivery system, comprising:
a container for storing a medicament prior to use, the container having a first end and a second end;
an injection member in fluid communication with the container;
an actuation mechanism associated with the container and configured to deliver the medicament from the container through the injection member when the actuation mechanism is activated; and
at least one detection element associated with the system; wherein in a first mode of operation of the system, medicament is delivered through the injection member and in a second mode of operation of the system, medicament is not delivered through the injection member after operation in the first mode has occurred, and the mode of operation is dependent on an output from the at least one detection element, said second mode of operation occurs based on input from the at least one detection element to detect removal of the injection member from a target site prior to completion of an injection.

5. The medicament delivery system of claim 4, further comprising a stopper that interacts with the actuation mechanism to deliver medicament when the actuation mechanism is activated by traversing the container from a first to a second position, and at least a first sensing element and a second sensing element, said second sensing element associated with the stopper, wherein the first sensing element senses a position of the second sensing element, and wherein an output is generated by the first sensing element, such that the mode of operation is dependent on an output received from the at least one detection element and the position of the stopper.

6. The medicament delivery system of claim 4, further comprising a controller configured to monitor the output from the at least one detection element, said controller configured to operate the system in one of the first mode of operation or the second mode of operation in response to the output received.

7. The medicament delivery system of claim 4, wherein the at least one detection element comprises a contact sensor, wherein the output generated by the at least one detection element is dependent on whether a contact is made between the contact sensor and a patient.

8. The medicament delivery system of claim 4, wherein the at least one detection element comprises a light sensor and the output is dependent on whether a light beam is projected from the container.

9. The medicament delivery system of claim 4, wherein the at least one detection element comprises a temperature sensor, and the output of the at least one detection element is dependent on a temperature of a skin of the patient detected by the temperature sensor.

10. The medicament delivery system of claim 4, wherein said at least one detection element comprises a contact sensor and a temperature sensor, wherein the mode of operation of the system is dependent on at least one output generated by the at least one detection element based on the contact sensor and the temperature sensor.

11. The medicament delivery system of claim 4, wherein the at least one detection element comprises a proximity sensor to detect a proximity of the system to a target area of a patient.

12. The medicament delivery system of claim 4, further comprising a valve, said valve being configured to open and close in response to the output generated by the at least one detection element.

13. The medicament delivery system of claim 4, wherein a locking mechanism is associated with the actuation mechanism, wherein the locking mechanism is initiated in response to the output generated by the at least one detection element.

14. The medicament delivery system of claim 13, wherein when the locking mechanism is in a locked position delivery of medicament through the injection member is prevented, and when the locking mechanism is in an unlocked position, medicament is delivered through the injection member.

15. The medicament delivery system of claim 4, further comprising a stopping mechanism, wherein the stopping mechanism is activated in response to an output generated by the at least one detection element and/or the at least a first sensing element, wherein the stopping mechanism is configured to halt delivery of the medicament after the actuation mechanism has been activated and before delivery of the medicament is complete.

16. The medicament delivery system of claim 6, wherein based on the output generated by the at least one detection element activation and/or inactivation of the actuation mechanism is electronically controlled by the controller.

17. The medicament delivery system of claim 4, wherein the system further comprises a flow sensor to detect an amount of medicament delivered through the injection member.

18. The medicament delivery system of claim 4, wherein the system comprises a visual indicator to indicate an amount of medicament in the container.

19. The medicament delivery system of claim 4, wherein the injection member is associated with the container such that it is extended from the container upon activation of the actuation mechanism, and retracted into the container after use.

20. The medicament delivery system of claim 19, further comprising an obstruction member, wherein upon retraction of the injection member into the container the obstruction member obstructs the injection opening such that extension of the injection member there through is prevented.

21. The medicament delivery system of claim 4, wherein a locking mechanism is associated with the actuation mechanism, wherein the locking mechanism is initiated in response to the output generated by the at least one detection element and at least a first sensing element.

22. The medicament delivery system of claim 17, wherein the mode of operation is dependent on an output from the at least one detection element and the flow sensor.

23. The medicament delivery system of claim 6, wherein the controller further comprises a timer component, and said mode of operation is dependent on an output from the at least one detection element and the timer component.

24. The medicament delivery system of claim 23, wherein the timer component detects initiation of actuation of the device, initiation of medicament delivery via the injection member, or completion of medicament delivery via the injection member, or a combination thereof.

25. The medicament delivery system of claim 5, wherein when at least one detection element detects a contact between the device and a patient, the system is in the first mode of operation, and wherein when the detection element detects no contact between the device and the patient, and the first sensing element senses the second sensing element is between the first and second position, the system is in the second mode of operation.

* * * * *